United States Patent
Osypka (10) Patent No.: US 7,421,295 B2
(45) Date of Patent: Sep. 2, 2008

(54) IMPLANTABLE CARDIAC LEAD HAVING REMOVABLE FLUID DELIVERY PORT

(75) Inventor: Thomas P. Osypka, Palm Harbor, FL (US)

(73) Assignee: Oscor Inc., Palm Harbor, FL (US)

( * ) Notice: Subject to any disclaimer, the term of this patent is extended or adjusted under 35 U.S.C. 154(b) by 516 days.

(21) Appl. No.: 10/623,200

(22) Filed: Jul. 18, 2003

(65) Prior Publication Data

US 2004/0054389 A1 Mar. 18, 2004

Related U.S. Application Data (60) Provisional application No. 60/397,047, filed on Jul. 19, 2002.

(51) Int. Cl.
*A61N 1/02* (2006.01)
*A61N 1/04* (2006.01)
(52) U.S. Cl. .......................... 607/37; 607/115; 607/120
(58) Field of Classification Search ............. 607/36–38, 607/115–123
See application file for complete search history.

(56) References Cited

U.S. PATENT DOCUMENTS

| | | | | |
|---|---|---|---|---|
| 4,350,169 | A | * | 9/1982 | Dutcher et al. ............... 607/119 |
| 5,458,631 | A | * | 10/1995 | Xavier ......................... 607/117 |
| 5,868,245 | A | * | 2/1999 | Alt .............................. 206/210 |
| 6,540,765 | B1 | | 4/2003 | Malacoff |
| 2002/0077683 | A1 | * | 6/2002 | Westlund et al. ............. 607/116 |
| 2002/0077684 | A1 | * | 6/2002 | Clemens et al. .............. 607/116 |

* cited by examiner

*Primary Examiner*—Carl H. Layno
*Assistant Examiner*—Tammie K. Heller
(74) *Attorney, Agent, or Firm*—Edwards Angell Palmer & Dodge LLP (57) ABSTRACT

An implantable cardiac lead includes an elongated lead body having opposed proximal and distal end portions, and a fluid delivery lumen extending therethrough. A connector assembly is operatively associated with the proximal end portion of the lead body. The connector assembly has a threaded engagement stem depending therefrom, and the lead includes a ported connector fitting having a body with a threaded engagement bore for threadably engaging the engagement stem. The body of the fitting has at least one passageway extending therethrough for communicating with the fluid delivery lumen of the lead body.

8 Claims, 6 Drawing Sheets

IMPLANTABLE CARDIAC LEAD HAVING REMOVABLE FLUID DELIVERY PORT

CROSS-REFERENCE TO RELATED APPLICATIONS

The subject application claims the benefit of priority to U.S. Provisional Patent Application Ser. No. 60/397,047 filed Jul. 19, 2002, which is incorporated herein by reference in its entirety.

BACKGROUND OF THE INVENTION

1. Field of the Invention

The subject invention is directed to implantable cardiac leads, and more particularly, to an implantable cardiac lead having a removable connector port for facilitating the introduction of an optical imaging fluid or therapeutic agent into a fluid delivery lumen extending through the lead body.

2. Background of the Related Art

Implantable cardiac stimulation leads, including epicardial and endocardial leads, are well known in the art. In general, these devices have an elongated flexible body with an electrode assembly at one end for contacting and stimulating cardiac tissue and a connector assembly at the other end for mating with an automated stimulation device, such as a pacemaker or defibrillator. The distal end of the lead can include a helical screw to facilitate active fixation of the lead tip or a plurality of flexible tines to facilitate passive fixation of the lead tip.

The implantation of a cardiac lead is often performed under vision with the aide of an imaging process such as fluoroscopy, angiography or optical densitometry using an optical contrast agent or dye. These imaging fluids are typically introduced to the lead implantation site by way of a catheter. For example, U.S. Pat. No. 6,540,765 to Malacoff discloses an apparatus for placing a pacing electrode in the coronary sinus of the heart which is defined by a catheter having a central lumen through which a lead is advanced for placement. A Tuohy-Borst multi-port adapter is provided at the proximal end of the catheter for receiving a dye. Once injected into the adapter, the dye travels through the lumen of the catheter into the coronary sinus through an exit port in the distal end of the catheter, and periodic angiograms are performed to assist in the proper placement of the lead.

The use of a catheter to facilitate the delivery of an optical imaging fluid such as a contrast agent or dye is not particularly cost effective and generally adds to the overall complexity of the lead implantation procedure. It would be beneficial therefore, to provide an implantable cardiac lead that is adapted and configured to effectuate the delivery of an optical imaging fluid to the site of lead implantation, without the, need of a catheter or similar assisting device.

SUMMARY OF THE INVENTION

The subject invention is directed to a new and useful implantable cardiac lead that includes an elongated lead body having opposed proximal and distal end portions, and at least one lumen which extends through the lead body to deliver an optical imaging fluid or therapeutic agent to the lead implantation site. The lead has an electrode assembly, which is operatively associated with the distal end portion of the lead body for stimulating cardiac tissue. The lead also has a connector assembly, which is operatively associated with the proximal end portion of the lead body for engaging a corresponding receptacle of a pacemaker or similar pulse generation device such as an implantable defibrillator. The connector assembly has an engagement stem depending therefrom, which is preferably threaded.

The cardiac lead of the subject invention further includes a ported connector fitting that has a body with an engagement bore provided at a distal end thereof, which is preferably threaded, for receiving the engagement stem of the connector assembly. The body of the connector fitting has at least one passageway extending therethrough, in communication with the engagement bore, for delivering fluid into a lumen of the lead body through the engagement stem of the connector assembly.

In one embodiment of the invention, the ported connector fitting has a bifurcated body with an engagement bore at a distal end thereof for receiving the engagement stem of the connector assembly. In this instance, the multi-ported connector fitting has a first passageway extending through a first portion of the bifurcated body, in communication with the engagement bore, for delivering a guidewire into the first lumen of the lead body through the engagement stem of the connector assembly. The multi-ported connector fitting has a second passageway extending through a second portion of the bifurcated body, in communication with the engagement bore, for delivering fluid into the second lumen of the lead body through the engagement stem of the connector assembly. Preferably, the two passageways formed in the ported connector fitting have funnel-shaped inlet regions to facilitate the introduction of a guidewire, stylet, hypodermic needle or similarly configured device into the passageway.

In one embodiment of the invention, the fluid delivery lumen of the lead body has an outlet port at the distal end of the lead body; In another embodiment, the fluid delivery lumen has an outlet port at a location spaced from the distal end of the lead body. In either instance the guidewire lumen preferably terminates within the distal end portion of the lead body.

Preferably, the electrode assembly of the cardiac lead is bipolar and includes a distal tip electrode defining an anode and a proximal ring electrode defining a cathode. Alternatively, the electrode assembly can be unipolar, tripolar or quadrupolar, as is well known in the art. The lead further includes a helical conductor coil, which is preferably a multifilar conductor coil, that extends through the lead body to connect the electrode assembly with the connector assembly. In one embodiment, the lead includes a helical fixation screw operatively associated with the distal end of the lead body for actively securing the lead to cardiac tissue. The helical fixation screw can be an advanceable screw driven by a screwdriver tipped stylet extended into the guidewire lumen. Alternatively, the lead can include a plurality of flexible tines for passively securing the lead to cardiac tissue.

These and other aspects of the cardiac lead of the subject invention will become more readily apparent to those having ordinary skill in the art from the following detailed description of the invention taken in conjunction with the drawings.

BRIEF DESCRIPTION OF THE DRAWINGS

So that those having ordinary skill in the art to which the subject invention pertains will more readily understand how to make and use the cardiac lead disclosed herein, embodiments thereof will be described in detail below with reference to the drawings, wherein.

DETAILED DESCRIPTION OF PREFERRED EMBODIMENTS

In the description which follows, the term "proximal" refers to the end of the cardiac lead which is farthest from the implantation site, while the term "distal" refers to the end of the cardiac lead which is nearest to the site of implantation.

Figures 1, 2:
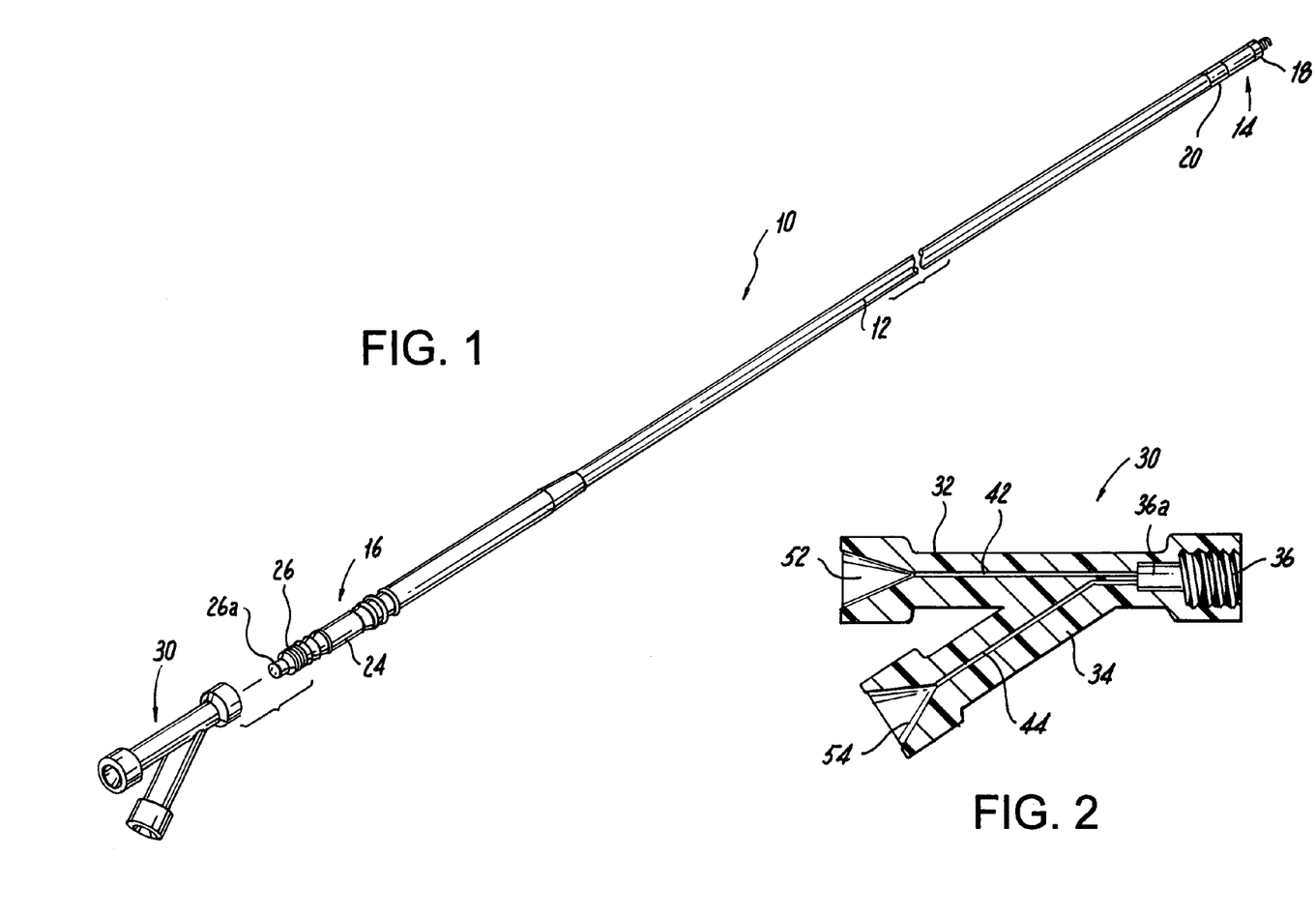
FIG. 1 is a perspective view of a cardiac lead constructed in accordance with a preferred embodiment of the subject invention and the bifurcated multi-ported connector fitting that is operatively associated with the proximal end thereof.
FIG. 2 is a cross-sectional view of the bifurcated multi-ported connector fitting shown in FIG. 1 illustrating the two passageways and threaded engagement bore that are formed therein.

Referring now to the drawings wherein like reference numerals identify similar structural elements of the apparatus disclosed herein, there is illustrated in FIG. 1 an implantable cardiac lead constructed in accordance with a preferred embodiment of the subject invention and designated generally by reference numeral 10. By way of example, cardiac lead 10 is illustrated in the form of a bipolar cardiac pacing lead adapted for active fixation. Those skilled in the art will readily appreciate that other types and configurations of cardiac leads can employ the same or similar unique and useful features of the cardiac lead 10 disclosed herein, including for example, a unipolar or multipolar cardiac pacing leads or implantable cardiac defibrillation leads.

Cardiac lead 10 includes an elongated flexible lead body 12 having a bipolar electrode assembly 14 operatively associated with a distal end thereof for stimulating cardiac tissue. Cardiac lead 10 further includes a connector assembly 16 operatively associated with the proximal end of the lead body 12 for communicating with a corresponding receptacle associated with a pulse generator or pacemaker (not shown). Lead body 12 is preferably formed from a biocompatible insulative material such as silicone rubber, polyurethane, or the like, and can range in length from 48 cm to 58 cm, with a diameter ranging up to 10 F. The bipolar electrode assembly 14 includes a distal tip electrode 18 that defines a cathode and a proximal ring electrode 20 that defines an anode. The electrodes are preferably formed from platinum, iridium or alloys thereof.

Figure 9:
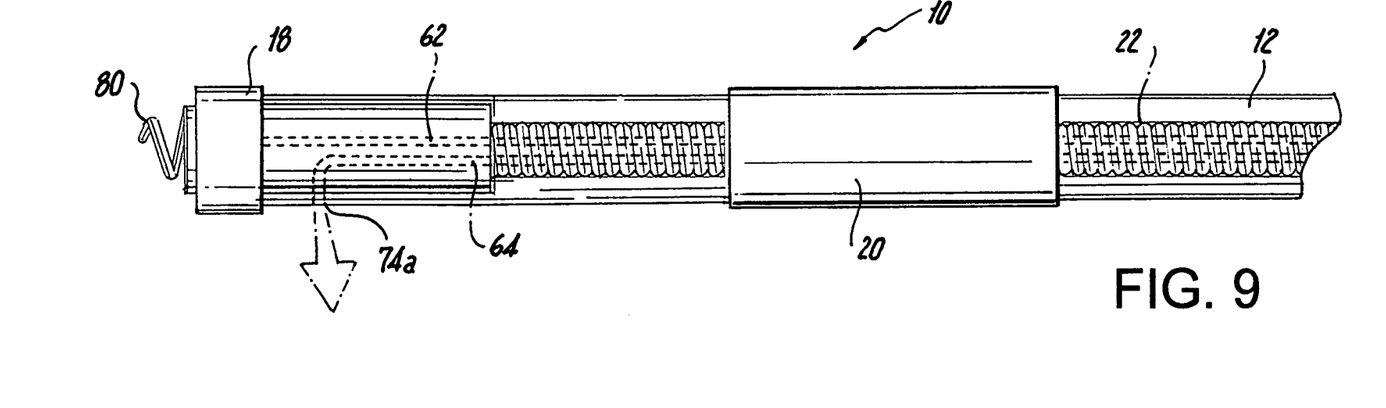
FIG. 9 is a side elevational view of the distal portion of the cardiac lead of FIG. 1 which illustrates, in phantom lines, the location of the outlet port of the fluid delivery lumen.
Figure 10:
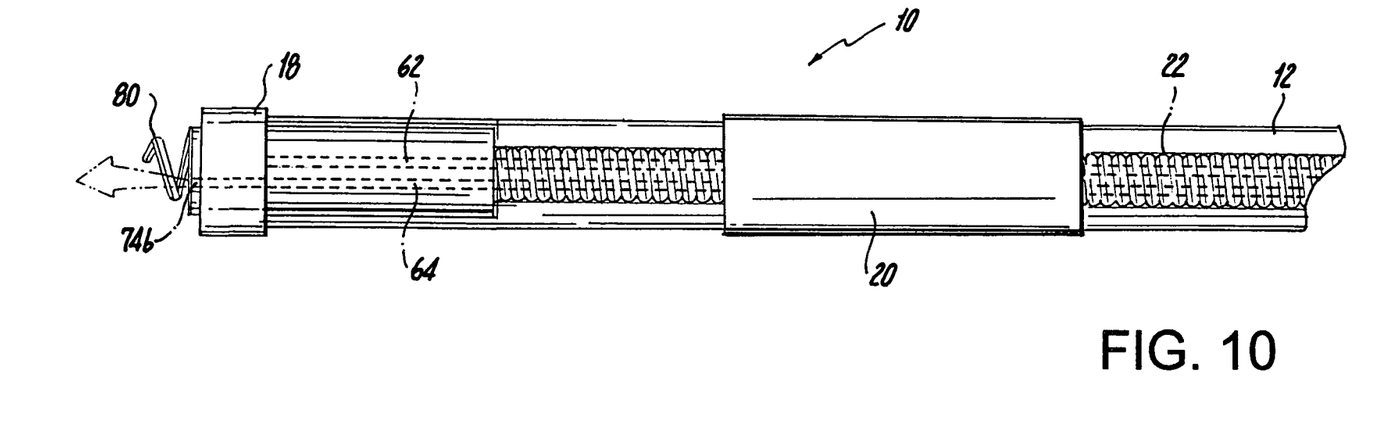
FIG. 10 is a side elevational view of the distal portion of the cardiac lead of FIG. 1 which illustrates, in phantom lines, an alternate location of the outlet port of the fluid delivery lumen.

Connector assembly 16 is electrically connected to the electrode assembly 14 by way of a conductor coil 22 that extends through the interior of the lead body 12 (see FIGS. 9 and 10). Preferably, conductor coil 22 is generally helical in configuration and includes one or more conductive wires or filaments formed from a material such as MP 35N. For example, the conductor coil 22 may be a multifilar conductor coil with as many as eight (8) filaments. A particularly useful multifilar conductor coil is disclosed in U.S. patent application Publication No. 2003/0092303, which is incorporated herein by reference in its entirety. Other conductors may be employed as well such as flexible low-ohm DFT drawn filled rope tubing.

Figure 3:
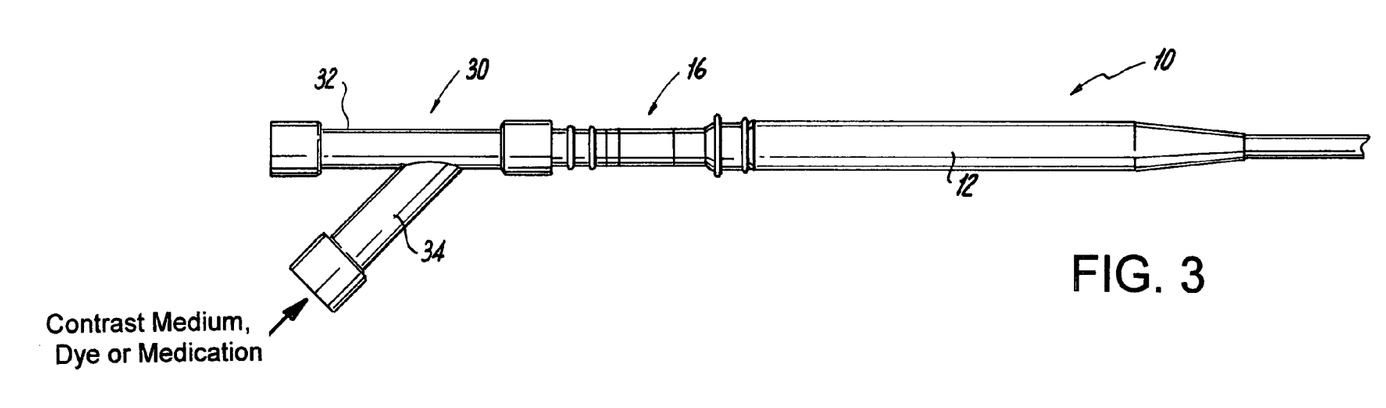
FIG. 3 is a side elevational view of the proximal end portion of the cardiac lead of FIG. 1 with the bifurcated multi-ported connector fitting threadably engaged therewith.

The connector assembly 16 is preferably formed from 316L stainless steel or a similar material and includes a primary connector portion 24 and a threaded engagement stem 26 that depends from the primary connector portion 24. The primary connector portion 24 may be configured as any standard type, size, or configuration of connector known in the art such as, for example, a bipolar IS-1 type connector (International Standard ISO 5841.3:1992). The threaded engagement stem 26 is adapted and configured to mate with a multi-ported connector fitting 30. As described in detail below, the multi-ported connector fitting 30 communicates with a pair of lumens that extend through the lead body 12 to facilitate the delivery of, among other things, optical imaging fluids to an exit port at the distal end of the lead body 12, as best seen in FIGS. 3 and 4.

Referring now to FIG. 2, multi-ported connector fitting 30 has a bifurcated body defined by main body portion 32, which has a central axis and a branch portion 34. The branch portion 34 extends at about a 30° angle to the central axis of the main body portion 32 of the fitting. A threaded engagement bore 36 is formed at the distal end of the main body portion 32 of fitting 30 for receiving and detachably engaging the threaded engagement stem 26 of connector assembly 16. Threaded engagement bore 36 is formed with a receptacle 36a for mating with the proximal tip 26a of threaded engagement stem 26. A main passageway 42 extends through the main body portion 32 of connector fitting 30, from a funnel shaped inlet port 52 to the receptacle 36a of engagement bore 36, to communicate with a guidewire/stylet lumen 62 formed in lead body 12, as shown in FIG. 4. Likewise, a secondary passageway 44 extends through the branch portion 34 of connector fitting 30, from a funnel shaped inlet port 54 to the receptacle 36a of engagement bore 36, to communicate with a fluid delivery lumen 64 formed in lead body 12, as shown in FIG. 4.

The funnel shape of inlet port 52 serves to ease the introduction of a guidewire wire or a positioning stylet into the main passageway 42 of fitting 30. Similarly, the funnel shape of inlet port 54 serves to ease the insertion of a needle or similar fluid injection device used to introduce a fluid into the secondary passageway 44 of fitting 30. The cooperating screw thread of the engagement bore 36 and the engagement stem 26 is specifically arranged so that the main passageway 42 and secondary passageway 44 of fitting 30 align respectively with the guidewire/stylet lumen 62 and fluid delivery lumen 64 upon threadably engaging the connector fitting 30 with the connector assembly 16.

Figure 4:
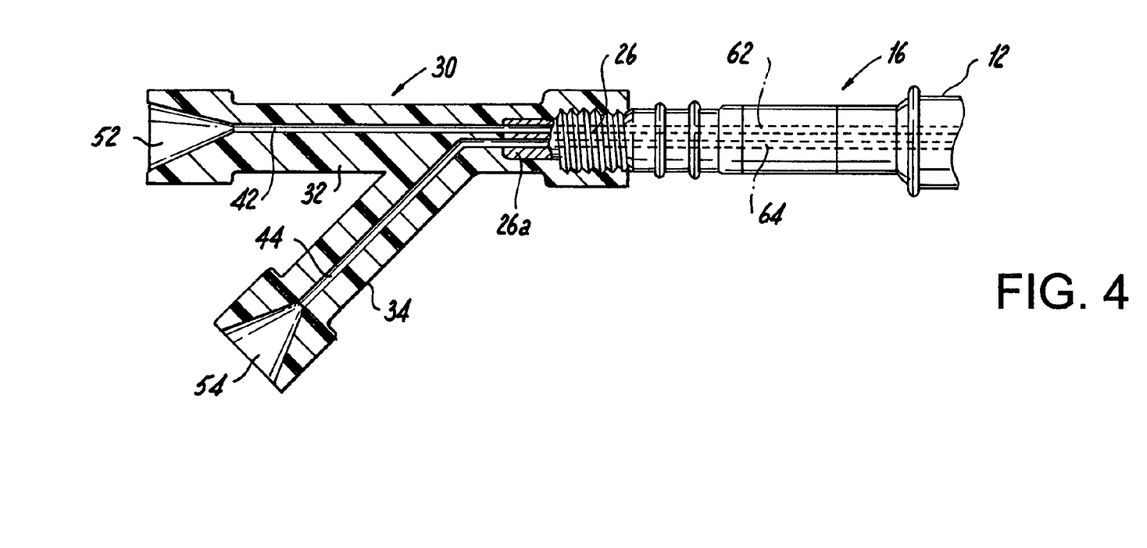
FIG. 4 is an enlarged cross-sectional view of the bifurcated multi-ported connector fitting threadably engaged with the connector assembly at the proximal end of the cardiac lead of FIG. 1.

As shown in FIGS. 1 and 4, the guidewire/stylet lumen 62 and fluid delivery lumen 64 of lead body 12 begin at the end of the proximal tip 26a of engagement stem 26, and extend through the interior of lead body 12, along the longitudinal axis thereof, to distal end portion of lead body 12. The guidewire/stylet lumen 62 preferably terminates within the lead body 12, while the fluid delivery lumen 64 terminates at an exit port 74a located at the distal end of lead body 12, as shown in FIG. 9. Alternatively, the fluid delivery lumen 64 terminates at an exit port 74b located in the side wall of the lead body 12 spaced proximal to the distal end of the lead body, as shown for example in FIG. 10.

It is envisioned that the guidewire/stylet lumen 62 would communicate with the helical fixation screw 80 operatively associated with the distal end of the lead body 12 (see FIGS. 9 and 10). Thus, a screwdriver tipped stylet can be passed through lead body 12, by way of a ported connector fitting, to manipulate the helical fixation screw 80 and actively secure the distal end of lead 10 to cardiac tissue during an implantation procedure.

Figures 5, 6:
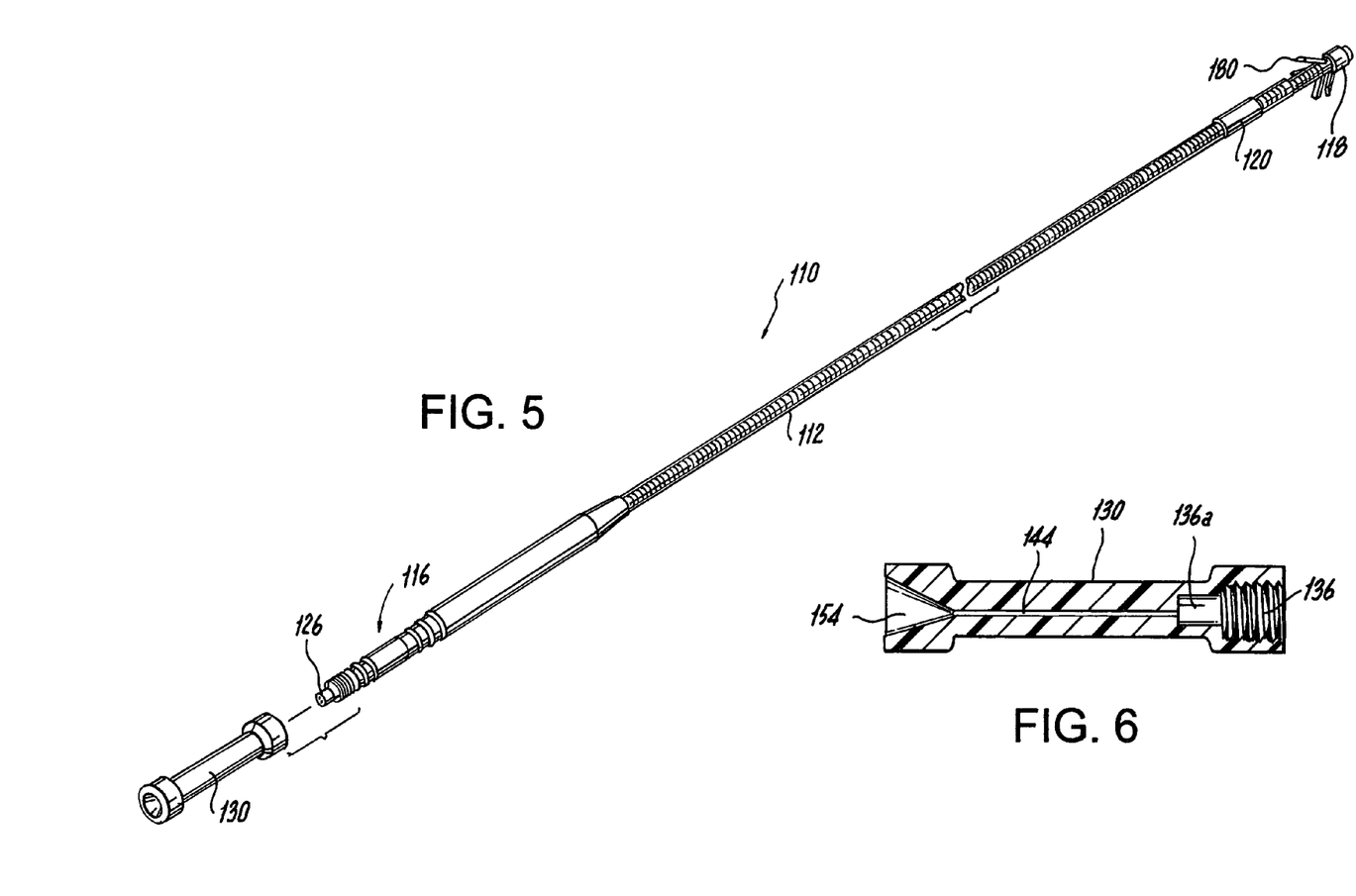
FIG. 5 is a perspective view of another cardiac lead constructed in accordance with a preferred embodiment of the subject invention, together with another embodiment of a uni-ported connector fitting that is operatively associated with the proximal end of the lead.
FIG. 6 is a cross-sectional view of the uni-ported connector fitting shown in FIG. 5 illustrating the passageway and threaded engagement bore that are formed therein.

Referring now to FIG. 5, there is illustrated another implantable cardiac lead constructed in accordance with a preferred embodiment of the subject invention and designated generally by reference numeral 110. Cardiac lead 110 differs from cardiac lead 10 in that it is configured for passive fixation rather than active fixation. Thus, the distal end operation of cardiac lead 110 includes a plurality of flexible tines 180 formed integral with the lead body 112 and disposed between the cathodic tip electrode 118 and the anodic ring electrode 120.

Figure 7:
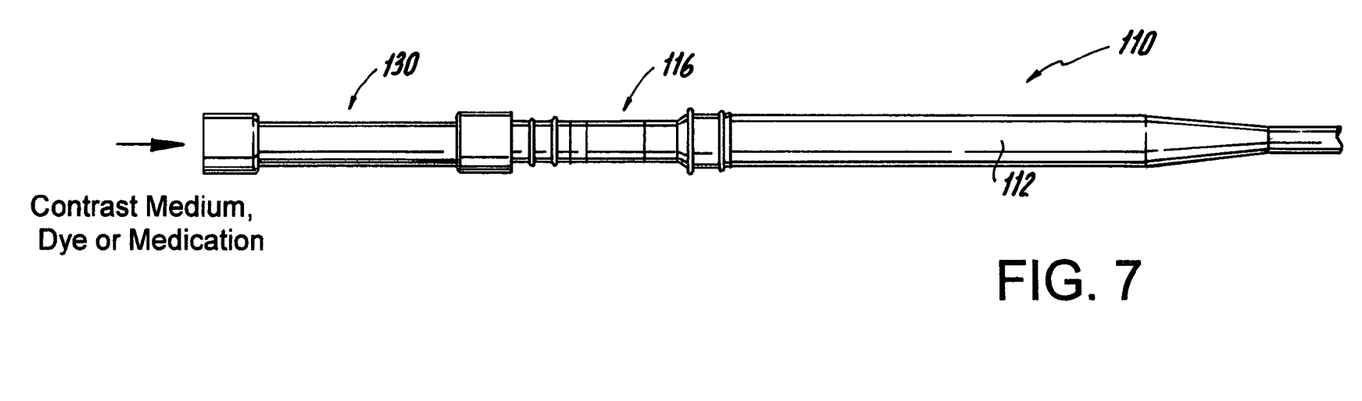
FIG. 7 is a side elevational view of the proximal end portion of the cardiac lead of FIG. 5 with the uni-ported connector fitting threadably engaged therewith.
Figure 8:
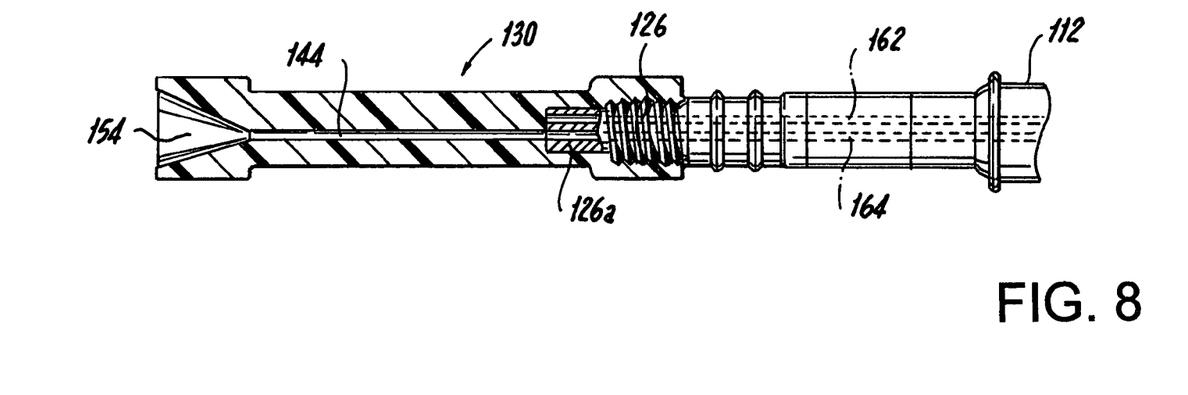
FIG. 8 is an enlarged cross-sectional view of the uni-ported connector fitting threadably engaged with the connector assembly at the proximal end of the cardiac lead of FIG. 5.

Referring to FIGS. 6 and 7, there is illustrated another ported connector fitting constructed in accordance with a preferred embodiment of the subject invention and designated generally by reference numeral 130. Connector fitting 130 differs from the multi-ported connector fitting 30 shown in FIGS. 1 and 2 in that it is uni-ported, and thus has a single passageway 144 which is adapted and configured to communicate with the fluid delivery lumen 164 of lead body 112, as best seen in FIG. 8. Passageway 144 has a funnel shaped inlet port 154 for receiving a fluid injection device and it communicates with the receptacle 136a of threaded engagement bore 136.

As illustrated in FIG. 8, when uni-ported connector fitting 130 is threadably engaged with the threaded engagement stem 126 of connector assembly 116, the passageway 144 is aligned with the fluid delivery lumen 164 of cardiac lead 110 which begins at the end of proximal tip 126a. At such a time, the guidewire/stylet lumen 162 of cardiac lead 110 is blocked and inaccessible.

Figure 11:
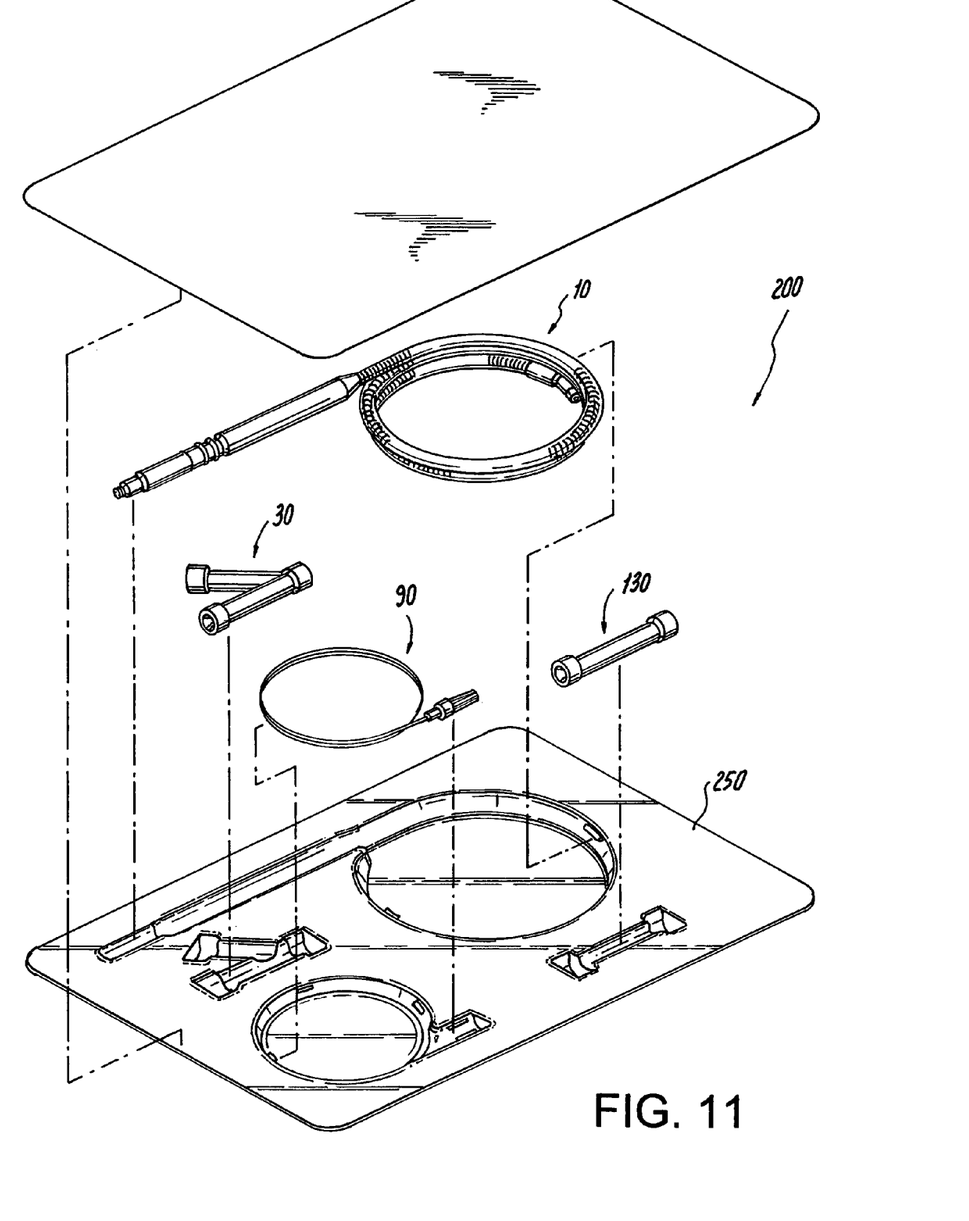
FIG. 11 is a perspective view of a kit containing a cardiac lead and the two types of ported connector fittings disclosed herein, along with a guidewire/stylet.

Referring now to FIG. 11, the subject invention is also directed to a lead implantation kit 200, which includes an implantable cardiac pacing lead, for example the cardiac lead 10 configured for active fixation, a bifurcated multi-ported connector fitting 30 and a uni-ported connector fitting 130. In addition, the kit 200 preferably includes a guidewire 90 for guiding the lead to the implantation site, and in this instance a screwdriver tipped stylet for manipulating the helical fixation screw to effect active fixation of the lead 10 to cardiac tissue. Where a lead configured for passive fixation is provided in the kit, such as cardiac lead 110, a screwdriver tipped stylet would not be included in kit 200. In either instance, a hermetically sealable preformed enclosure 250 is provided for housing each of the components of the kit.

As noted above, the fluid delivery lumen of the cardiac lead of the subject invention is preferably adapted to deliver an optical imaging fluid or optical contrast agent to the distal end of the lead body. For example, a fluoroscopic dye may be introduced into fluid delivery lumen to facilitate the accurate positioning of the electrode assembly of the cardiac lead at the implantation site. Exemplary contrast agents or dyes include Indocyanine Green (ICG), fluorescein isothiocyanate, silver compounds such as silver nitrate, rose bengal, nile blue and Evans Blue, Sudan III, Sudan Black B and India Ink.

It is also envisioned that the fluid delivery lumen of the cardiac lead of the subject invention can be used to deliver a therapeutic fluid or medicament to the implantation site. Such drugs may include anti-inflammatory drugs such as steroids, including for example, dexamethosone sodium phosphate and dexamethasone sodium acetate. Other non-steroid based drugs can also be delivered through the fluid delivery lumen of the lead.

Although the implantable cardiac lead of the subject invention has been described with respect to preferred embodiments, those skilled in the art will readily appreciate that changes and modifications may be made thereto without departing from the spirit and scope of the subject invention as defined by the appended claims.

What is claimed is:

1. An implantable cardiac lead comprising:
  a) an elongated lead body having opposed proximal and distal end portions and having a guidewire lumen and a fluid delivery lumen extending therethrough;
  b) an electrode assembly operatively associated with the distal end portion of the lead body for stimulating cardiac tissue;
  c) a connector assembly operatively associated with the proximal end portion of the lead body for engaging a corresponding receptacle of a pulse generating device, the connector assembly having an engagement stem depending proximally therefrom, wherein the guidewire lumen and the fluid delivery lumen of the lead body extend through the engagement stem of the connector assembly, and wherein the engagement stem includes a proximal tip portion and a threaded engagement portion integrally formed with the engagement stem, longitudinally distal to the proximal tip portion thereof; and
  d) a detachable ported connector fitting having a main body portion and a branch portion which extends from the main body portion, wherein the main body portion has an engagement bore at a distal end thereof for receiving the engagement stem of the connector assembly, the engagement bore having a proximal receiving section configured to receive the proximal tip portion of the engagement stem and a threaded engaging section longitudinally distal to the proximal receiving section of the engagement bore and configured to engage the threaded engagement portion of the engagement stem, the main body portion of the ported connector fitting having a primary passageway extending therethrough to align and communicate with the guidewire lumen of the lead body through the engagement stem of the connector assembly, and the branch portion of the ported connector fitting having a secondary passageway extending therethrough to align and communicate with the fluid delivery lumen of the lead body through the engagement stem of the connector assembly, when the ported connector fitting is threadably engaged with the connector assembly.

2. An implantable cardiac lead as recited in claim 1, wherein the primary and secondary passageways formed in the ported connector fitting each have a funnel-shaped inlet region.

3. An implantable cardiac lead as recited in claim 1, wherein the fluid delivery lumen formed in the lead body has an outlet port at the distal end of the lead body.

4. An implantable cardiac lead as recited in claim 1, wherein the fluid delivery lumen formed in the lead body has an outlet port at a location spaced from the distal end of the lead body.

5. An implantable cardiac lead as recited in claim 1, wherein the electrode assembly is bipolar and includes a distal tip electrode and a proximal ring electrode.

6. An implantable cardiac lead as recited in claim 1, further comprising a helical conductor coil extending through the lead body for connecting the electrode assembly with the connector assembly.

7. An implantable cardiac lead as recited in claim 1, further comprising a helical fixation screw operatively associated with the distal end of the lead body for actively securing the lead to cardiac tissue.

8. An implantable cardiac lead as recited in claim 1, further comprising a plurality of flexible tines provided at the distal end of the lead body for passively securing the lead to cardiac tissue.

* * * * *